(12) United States Patent
Takeuchi et al.

(10) Patent No.: US 6,824,852 B2
(45) Date of Patent: Nov. 30, 2004

(54) LAMINATED HEATING BODY

(75) Inventors: Naohito Takeuchi, Kagawa (JP); Kiyoshi Miyazawa, Kagawa (JP); Mitsuko Yamaji, Kagawa (JP); Ayami Suga, Kagawa (JP); Toshiyuki Tanio, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 76 days.

(21) Appl. No.: 10/351,224

(22) Filed: Jan. 24, 2003

(65) Prior Publication Data

US 2003/0143347 A1 Jul. 31, 2003

(30) Foreign Application Priority Data

Jan. 31, 2002 (JP) .................................. 2002-023263

(51) Int. Cl.[7] .................................................. A61F 17/56
(52) U.S. Cl. ...................... 428/76; 428/444; 428/457; 428/702
(58) Field of Search ..................... 428/76, 444, 457, 428/702, 34.1

(56) References Cited

U.S. PATENT DOCUMENTS 3,643,665 A    2/1972  Caillouette
4,925,743 A    5/1990  Ikeda et al.

FOREIGN PATENT DOCUMENTS

JP    04-300542 A1    10/1992

*Primary Examiner*—Sandra M. Nolan
(74) *Attorney, Agent, or Firm*—Darby & Darby

(57) ABSTRACT

A heat conductivity from a heating body to a user's skin is improved to provide satisfactorily warm feeling to the skin of the user. A laminated heating body has a heating body and a cover sheet covering the heating body. The cover sheet defines at least one low temperature portion formed from a material having low heat conductivity and at least one high temperature portion formed from a material having high heat conductivity. The at least one low temperature portion and the at least one high temperature portion are formed separately on a surface of the cover sheet contacting with a user's skin.

5 Claims, 3 Drawing Sheets

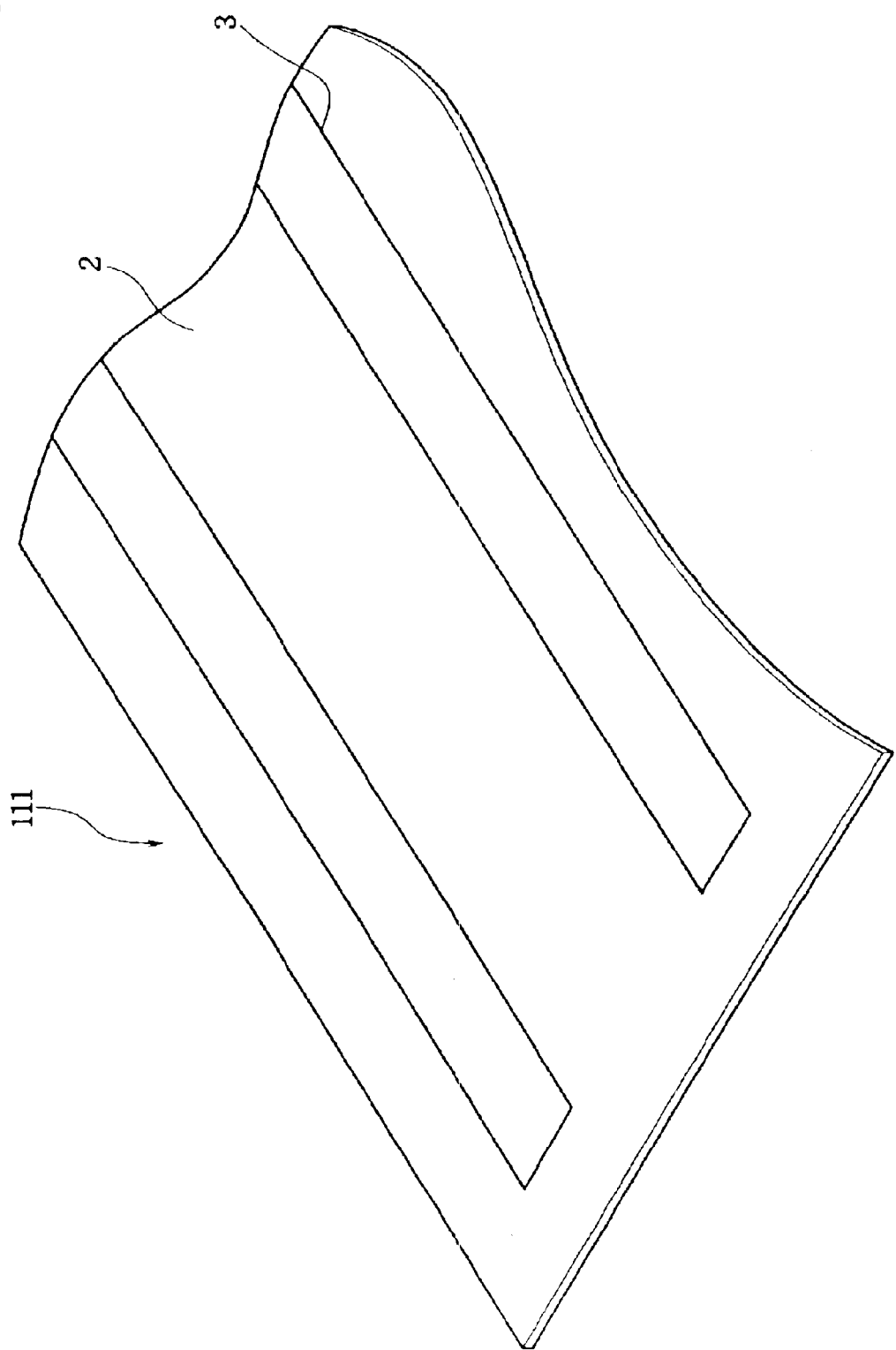

LAMINATED HEATING BODY

CROSS REFERENCE TO THE RELATED APPLICATION

The present application has been filed with claiming priority based on Japanese Patent Application No. 2002-23263, filed on Jan. 31, 2002. Disclosure of the above-identified Japanese Patent Application is herein incorporated by reference.

BACKGROUND OF THE INVENTION

1. Field of the Invention

The present invention relates generally to a laminated heating body, such as a disposable warmer or the like. More particularly, the invention relates to a laminated heating body having a cover sheet covering a heating body and including a portion having heat conductivity different from that of remaining portion.

2. Description of the Related Art

A warmer, such as a disposable warmer, is a laminate body of a heating body and a cover sheet wrapping the heating body. The cover sheet is typically formed into a bag shape for achieving a function for sealingly enclosing the heating body received therein and a function for transmitting heat generated from the heating body to a user's skin. In case of the conventional disposable warmer, the cover sheet is formed from non-woven fabric or the like.

On the other hand, in Japanese Unexamined Patent Publication No. Heisei 4 (1992)-300542, a disposable warmer is disclosed, in which a heat conducting medium is disposed between the heating body and the cover sheet covering the former.

The disposable warmer disclosed in the above-identified publication has the heating body disposed between an upper non-woven fabric and a lower non-woven fabric. A film form heatconducting medium is disposed between the heating body and the lower non-woven fabric. Area of the film form heat conducting medium is wider than area of the heating body.

In the disposable warmer disclosed in the above-identified publication, heat generated by the heating body can be transmitted to wider area by means of the film form heat conducting medium to widen heat source. Also, a thickness of the body of the disposable warmer can be reduced.

However, conventionally, the disposable warmer, in which the heating body is covered with the non-woven fabric, encounters shortcoming in low heat transmission efficiency to transmit heat generated by the heating body to the skin of the user.

On the other hand, in the disposable warmer disclosed in the above-identified publication, while it can widen range to transmit the heat generated by the heating body, since widely distributed heat is transmitted to the skin of the user through the non-woven fabric, heat transmission efficiency to the user's skin is still low to be unsatisfactory for providing warm feeling for the skin of the user over wide range.

SUMMARY OF THE INVENTION

The present invention has been worked out in view of the shortcoming in the prior art set forth above. It is therefore an object of the present invention to provide a laminated heating body, in which heat conductivity from a heating body to a user's skin is improved to provide satisfactorily warm feeling to the skin of the user.

According to one aspect of the present invention, a laminated heating body comprises:

a heating body; and a cover sheet covering the heating body, the cover sheet defining at least one low temperature portion formed from a material having low heat conductivity and at least one high temperature portion formed from a material having high heat conductivity, the at least one low temperature portion and the at least one high temperature portion being formed separately on a surface of the cover sheet contacting with a user's skin.

In the laminated heating body according to the present invention, heat generated by the heating body is efficiently transmitted to the user's skin through the high temperature portion formed of a material having high heat conductivity. Since the cover sheet maintains temperature difference between the high temperature portion and the low temperature portion, excessive heat should not be applied to the user's skin. Thus, appropriately high and comfortable temperature can be applied to the user's skin. Also, since heat can be easily transmitted to the user's skin from the high temperature portion, the user may feel as if skin is warmed in wide area.

For example, the cover sheet may be consisted of a sheet base and a heat conductive member fitted on a plurality of portions of the sheet base and having higher heat conductivity than the sheet base, the sheet base forms the low temperature portion and the heat conductive member forms the high temperature portion. The heat conductive member may be at least one of a metal plate or a metal foil. The cover sheet may also be consisted of a sheet base and at least one kind of metal plate or metal foil fitted on a plurality of portions of the sheet base, the sheet base forms the low temperature portion and each of the metal plate or the metal foil forms at least one kind of the high temperature portion.

The metal plates or metal foils fitted on various portions on the sheet base can be formed of the same metal. In the alternative, the metal plates or metal foils to be fitted on various portions on the sheet base can be formed of different metals. By forming the metal plates or metal foils of different metals, temperatures at respective high temperature portions can be differentiated. In this case, different portions of the user's skin are warmed at mutually different temperatures. This may give the user to be warmed uniformly in wide area.

For example, the sheet base may be formed from a non-woven fabric or a woven fabric.

On the other hand, in the cover sheet, the sheet base is placed in opposition to the heating body, and the metal plate or the metal foil is located on a surface of the sheet base remote from the heating body. The metal plate or the metal foil may be directly opposing to the heating body. The sheet base may be formed with openings, and the metal plates or the metal foils may be arranged at portions of the openings.

As set forth above, the metal plate or the metal foil may be arranged on the surface of the sheet base remote from the heating body, or in the alternative, in direct contact with the heating body depending upon high and low of the heat conductivity. Depending upon nature of the heating body or heat conductivity of the metal plate or metal foil, heat transmission to the user's skin can be optimized.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings:

FIG. 4 is a perspective view showing a further embodiment of a cover sheet.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure is not shown in detail in order to avoid unnecessary obscurity of the present invention.

Figure 1:
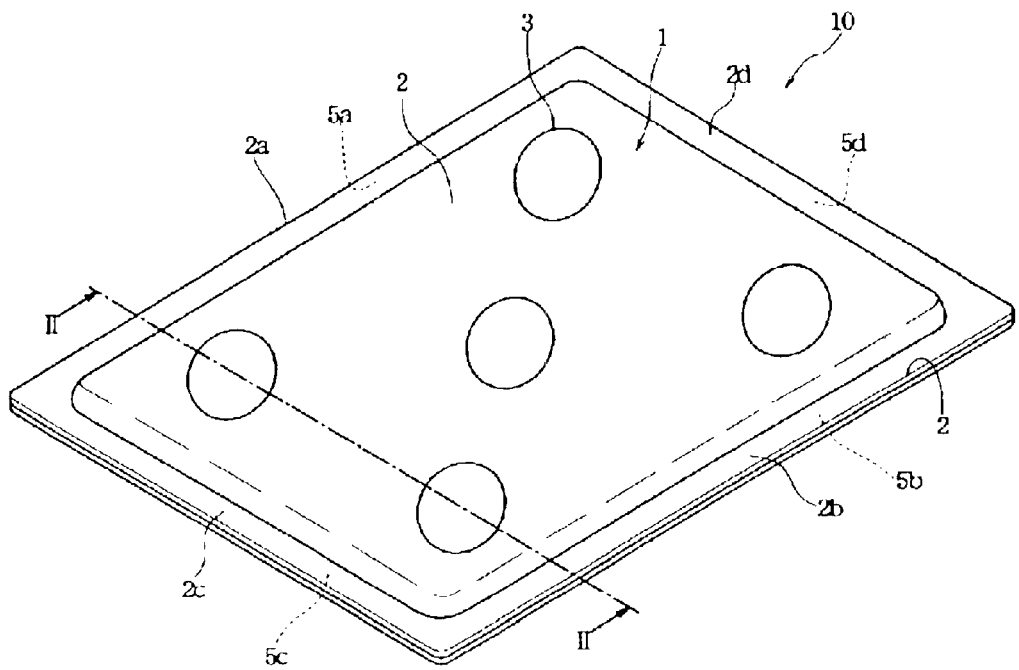
FIG. 1 is a partial perspective view showing the preferred embodiment of a laminated heating body according to the present invention.
Figure 2:
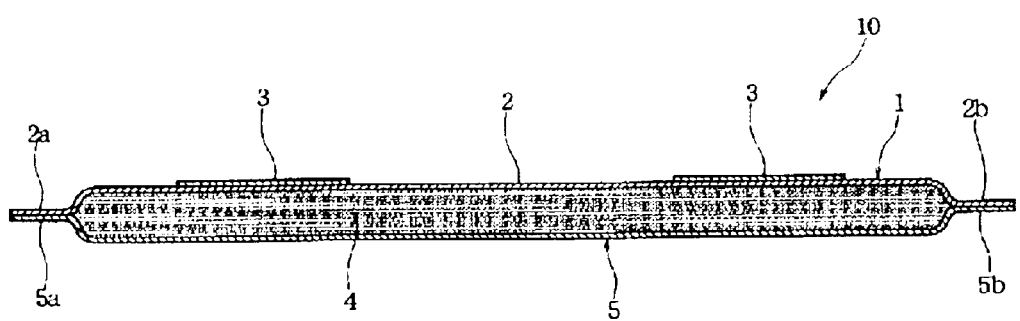
FIG. 2 is a section of the laminated heating body taken along line II—II of FIG. 1.

FIG. 1 is a partial perspective view showing the preferred embodiment of a laminated heating body according to the present invention, and FIG. 2 is a section of the laminated heating body taken along line II—II of FIG. 1.

A laminated heating body 10 shown in FIGS. 1 and 2 is applicable for a disposable warmer or the like. The shown embodiment of the laminated heating body 10 includes a heating body 4, a cover sheet 1 covering a front side surface of the heating body 4, and a back sheet 5 covering a back side surface of the heating body 4.

The heating body 4 is formed by mixing metal powder, such as iron powder or the like, reaction auxiliary agent, such as sodium chloride or the like, activated charcoal, water, moisture holding agent and so forth.

In the condition where the heating body 4 is disposed between the cover sheet 1 and the back sheet 5, a right side edge 2a of the cover sheet 1 and a right side edge 5a of the back sheet 5, a left side edge 2b of the cover sheet 1 and a left side edge 5b of the back sheet 5, a front edge 2c of the cover sheet 1 and a front edge 5c of the back sheet 5, and a rear edge 2d of the cover sheet 1 and a rear edge 5d of the back sheet 5 are bonded by hot melt adhesive, heat seal and so forth, respectively.

The cover sheet 1 is consisted of a sheet base 2 and a heat conductive member 3. The sheet base 2 is a non-woven fabric sheet, a woven fabric sheet, a resin sheet and so forth. When the sheet base 2 is formed from non-woven fabric, spun-bonded non-woven fabric fabricated from polypropylene fibers; a laminated sheet in which the spun-bonded non-woven fabric and melt-blown non-woven fabric fabricated from polypropylene fibers are laminated in a sequential order of spun-bonded non-woven fabric/melt-blown non-woven fabric/spun-bonded non-woven fabric; spun-laced non-woven fabric fabricated by entangling fibers by applying high pressure water jet to the fibrous web formed from polyester fibers, polypropylene fibers and rayon fibers and so forth, may be used as the non-woven fabric forming the sheet base 2.

The heat conductive member 3 may be a metal plate or a metal foil formed from a metal having relatively high heat conductivity. The metal may be selected among gold, silver, copper, chromium, aluminum, magnesium, molybdenum, zinc, tungsten, cadmium, nickel, rhodium, iron and so forth or an alloy of two or more metals.

On the other hand, the heat conductive member 3 is simply required to have higher heat conductivity than the sheet base 2, and can be a sheet form heat-resistant resin, such as polypropylene, polyethylene terephthalate, polyphenyl sulfide and the like blended with fillers such as the metal selected among the foregoing group. It is also possible to use a non-wove fabric or woven fabric fabricated from a composite fiber consisted of metal fibers and the foregoing resin.

In the embodiment shown in FIGS. 1 and 2, the heat conductive member 3 is circular shape. The heat conductive member 3 is bonded on the front surface of the sheet base 2 by an anaerobic adhesive or other heat-resistant adhesive. As a result, in the cover sheet 1, the heat conductive member 3 having high heat conductivity is present on the front surface of the sheet base 2 having relatively low heat conductivity in a condition where occupied regions are defined.

Throughout the disclosure, "heat conductivity" means a ratio of a heat flow flowing through a unit area in an isothermal surface within a substance in a direction perpendicular thereto in a unit period and a temperature gradient in the flow direction of the heat flow. Accordingly, when heat is applied to the cover sheet 1 from the heating body 4 under the same condition, a temperature on the surface of the heat conductive member 3 becomes higher than a temperature on the surface of the sheet base 2 after predetermined period of time.

In the shown embodiment, the surface of the sheet base 2 becomes a low temperature portion and the surface of the heat conductive portion 3 becomes a high temperature portion to cause temperature difference between the low temperature portion and the high temperature portion. It should be noted that the materials of all heat conductive members 3 located at a plurality of positions may be the same material, or, in the alternative, the material of the heat conductive member located at the center portion can be differentiated from the material of the heat conductive members located at circumferential portions. When the heat conductive members 3 are formed of two or more kinds of different materials, the surface temperatures of the heat conductive materials 3 may be different depending upon the materials thereof. Therefore, in this case, two or more of high temperature portions having respectively different surface temperature are formed.

On the other hand, when the sheet base 2 forming the low temperature portion is formed from gas permeable non-woven fabric, air can be supplied to the heating body 4 through the sheet base 2 to promote heating of the heating body 4 by oxidation reaction.

It is preferred that when heat is generated by the heating body 4 and the generated heat is applied to the cover sheet 1, a temperature difference between the surface of the sheet base 2 and the surface of the heat conductive member 3 is within a range of 1 to 4° C. after 60 minutes from starting of heating of the heating body 4. Such temperature difference between the sheet base 2 and the heat conductive members 3 provides temperature gradient on the surface of the cover sheet contacting with the user's skin. When the temperature difference between the sheet base 2 and the heat conductive members 3 is greater than or equal to 1° C., temperature gradient on the surface of the cover sheet becomes sufficient to prevent dulling of temperature sensitivity of the skin when the cover sheet 1 is contacted on the skin of the user as surface member of the warmer, and thus to maintain warm feeling of the user for a long period. On the other hand, if the temperature difference is smaller than 1° C., the user's skin may be easily dulled to loose warm feeling in a short period. If the temperature difference is smaller than 4° C., the user's skin may not be excessively heated.

Next, the back sheet 5 is formed from a resin sheet. It should be noted that the back sheet 5 has gas permeability so as to promote oxidation reaction of the internal heating body 4 for heating. For example, the back sheet 5 may be produced by melt extrusion of polypropylene resin or polyethylene resin blended with inorganic fillers into a film to form pores in the portion of the inorganic fillers. In the alternative, the back sheet 5 may be formed by the same non-woven fabric as the sheet base 2. In the further alternative, the back sheet 5 may be formed by a combination of the sheet base 2 and the heat conductive members 3 similarly to the cover sheet 1.

The laminated heating body 10 is sealingly enclosed in a gas impermeable film package before use. By opening the film package, air is supplied to the heating body 4 through the sheet base 2 and/or the back sheet 5 to cause oxidation reaction in the heating body 4.

In the cover sheet 1 appearing on the surface, the low temperature portion on the surface of the sheet base 2 and the high temperature portions on the surface of the heat conductive members 3 are separately defined on the sheet surface to provide temperature difference between the low temperature portion and the high temperature portions. Therefore, even when the cover sheet 1 is held in contact with the user's skin for a long period, temperature sensitivity of the skin may not be dulled to provide comfortably warm feeling to the user. Also, since heat can be easily transmitted from the high temperature portions to the user's skin, the user may feel that the skin is warmed in the wide area to enhance warming effect.

Figure 3:
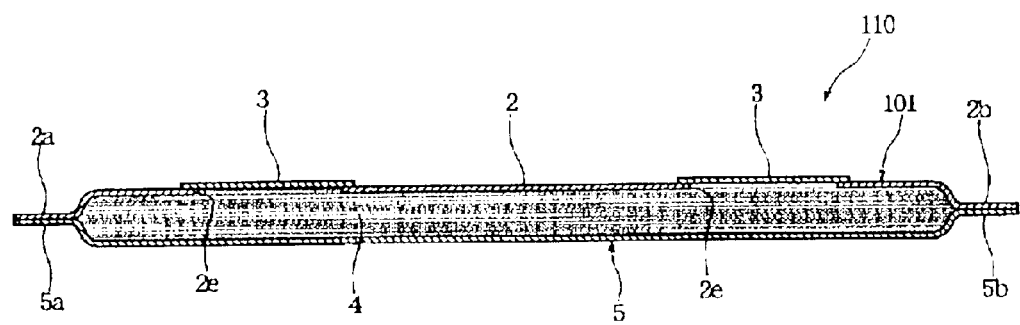
FIG. 3 is a section showing the second embodiment of a laminated heating body according to the present invention.

FIG. 3 is a section showing the second embodiment of the laminated heating body according to the present invention.

In the second embodiment shown in FIG. 3, like components to those in FIGS. 1 and 2 will be identified by like reference numerals and detailed description for the common components to those in FIGS. 1 and 2 will be eliminated for avoiding redundant description to keep the disclosure simple enough to facilitate clear understanding of the present invention.

A cover sheet 101 of a laminated heating body 110 shown in FIG. 3 has the sheet base 2 formed with openings 2e. The heat conductive members 3 are secured by bonding on the surface of the sheet base 2 in such a manner that the heat conductive members 3 cover the openings 2e.

In the shown embodiment of the laminated heating body 110, the heat conductive members 3 directly contact with the heating body 4 without interpositioning the sheet base 2. With this arrangement, better heat transmission efficiency from the heating body 4 to the heat conductive members 3 than that in the former embodiment can be achieved. It is possible that heat generated by the heating body 4 is transmitted to the sheet base 2 via the heat conductive members 3 to form high temperature portions at the portions where the heat conductive members are provided.

In the further alternative embodiment, as shown in FIG. 4, each of the heat conductive members 3 is formed into a stripe form. The stripe form heat conductive members 3 are boned on either surface (i.e., an internal surface or an external surface) of the sheet base 2 to form a cover sheet 111. In the still further alternative, the stripe form heat conductive members 3 may be bonded with covering slit form openings formed in the sheet base 2 or with covering a plurality of openings formed in the sheet base 2 in alignment in a longitudinal direction of the heat conductive members 3.

Namely, in each laminated heating body 10, 110, depending upon heat conductivity of the sheet base 2 or heat generation amount of the heating body 4, material, shape or size of the heat conductive member 3 is selected to select fitting on the surface of the sheet base 2 or directly on the heating body 4 for optimizing temperature difference between the high temperature portion and the low temperature portion on the surface of each cover sheet 1, 101, 111.

EXAMPLE

The laminated heating body 10 having structure shown in FIGS. 1 and 2 was formed.

The sheet base 2 was formed from a laminated sheet of a spun-bonded non-woven fabric of nylon fibers to have basis weight of 35 g/m$^2$ and a moisture impermeable polyethylene film of 60 $\mu$m thick. Total basis weight of the laminated sheet was 118 g/m$^2$.

The heat conductive member 3 was formed by laminating a PET film of 12 $\mu$m thick, aluminum foil of 12 $\mu$m thick and uniaxially stretched PP film of 30 $\mu$m thick by adhesive. A total thickness of the heat conductive film excluding adhesive layer was 54 $\mu$m. A diameter of the heat conductive film was 50 mm.

The back sheet 5 was formed from a laminated sheet of a spun-bonded non-woven fabric of nylon fibers to have basis weight of 35 g/m$^2$ and a moisture permeable polyethylene film of 60 $\mu$m thick. The back sheet having total basis weight of 116 g/m$^2$ was used. A moisture permeability as measured according to JIS-K7129 (Testing methods for water vapor transmission rate of plastic film and sheeting (instrument method)) was 431 ml/m$^2 \cdot$day.

On the other hand, as the heating body 4, "Hokaron" (trade name) available from Lotte Denshi Kogyo Kabushiki Kaisha was used.

The surface temperature of the laminated heating body 10 was measured by a temperature measurement device (Thermo-recorder "RT-10": Tabai Espec Kabushiki Kaisha). A gauge head of the temperature measurement device was contacted on the surface of the sheet base 2 and the surface of the heat conductive member 3. Then, the laminated heating body 10 was wrapped with a four-fold towel and temperatures of the surfaces of the sheet base 2 and the heat conductive member 3 were measured at respective timings set out below. An environment of measurement was 25° C. in temperature and 65% in relative humidity.

At timings of 60, 300 and 600 minutes after starting heating, the surface temperature of the sheet base 2 was 48.7° C., 49.8° C. and 43.7° C., respectively, and the surface temperature of the heat conductive member 3 was 50.1° C., 51.8° C. and 48.5° C., respectively.

On the other hand, when the laminated heating body 110 of FIG. 3 was produced using the same materials, the surface temperatures were measured at the same timings. At timings of 60, 300 and 600 minutes after starting heating, the surface temperature of the sheet base 2 was 48.7° C., 49.8° C. and 43.7° C., respectively, and the surface temperature of the heat conductive member 3 was 51.5° C., 53.0° C. and 49.7° C., respectively.

As set forth above, the laminated heating body according to the present invention is suitable for use as the warmer, such as a disposable warmer or the like. In this case, by providing temperature difference on the sheet surface, warm feeling can be provided for the skin of the user for a long period to maintain comfortable use feeling.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

For instance, it is possible to form the sheet base of the cover sheet with a plurality of sheet bases having mutually different heat conductivity and to permit partial removal of one sheet base from the other for providing local temperature difference on the surface of the cover sheet. The cover sheet consisted of a plurality of sheet bases has been disclosed or suggested in commonly assigned co-pending U.S. Patent Application, for "Laminated Heating Body", filed with claiming the convention priority based on Japanese Patent Application No. 2002-23267, filed on Jan. 31, 2002. The disclosure of the above-identified co-pending U.S. Patent Application is herein incorporated by reference.

What is claimed is:

1. A laminated heating body comprising:

a heating body; and a cover sheet over the heating body, the cover sheet having a surface that contacts a user's skin and that has low and high temperature portions, wherein the surface of the cover sheet is composed of a sheet base and a plurality o heat conductive members formed from a plate of foil of metal that has higher heat conductivity than the sheet base so that the heat conductive members form a high temperature portion and the sheet base forms a low temperature portion.

2. A laminated heating body as set forth in claim 1, wherein said sheet base is formed from a non-woven fabric or a woven fabric.

3. A laminated heating body as set forth in claim 1, wherein in said cover sheet, said sheet base is placed in opposition to said heating body, and said heat conductive members are located on a surface of said sheet base remote from said heating body.

4. A laminated heating body as set forth in claim 3, wherein said heat conductive members are directly opposed to said heating body.

5. A laminated heating body as set forth in claim 4, wherein said sheet base is formed with openings, and said heat conductive members are arranged to cover said openings.

* * * * *